(12) United States Patent
Hodge

(10) Patent No.: US 6,851,295 B2
(45) Date of Patent: Feb. 8, 2005

(54) CHECK ROD

(75) Inventor: Oliver Daniel Hodge, Winslow (GB)

(73) Assignee: Molins, plc, Milton Keynes (GB)

( * ) Notice: Subject to any disclaimer, the term of this patent is extended or adjusted under 35 U.S.C. 154(b) by 0 days.

(21) Appl. No.: 10/312,067

(22) PCT Filed: Jun. 20, 2001

(86) PCT No.: PCT/GB01/02713
§ 371 (c)(1),
(2), (4) Date: Jul. 7, 2003

(87) PCT Pub. No.: WO01/97639
PCT Pub. Date: Dec. 27, 2001

(65) Prior Publication Data
US 2004/0025562 A1 Feb. 12, 2004

(30) Foreign Application Priority Data
Jun. 20, 2000 (GB) .............................. 0015093

(51) Int. Cl.[7] .............................................. G01N 15/06
(52) U.S. Cl. ........................... 73/1.01; 73/1.16; 73/1.57
(58) Field of Search ................................. 73/1.01, 1.16, 73/1.35, 1.57, 37, 38

(56) References Cited
U.S. PATENT DOCUMENTS

| T940,004 I4 | * | 11/1975 | Dixon | ......................... 73/1.35 |
| 4,155,248 A | * | 5/1979 | Wagner et al. | .................. 73/38 |
| 4,341,109 A | * | 7/1982 | Evans, Jr. | ....................... 73/37 |
| 5,719,328 A | * | 2/1998 | Gombash, Jr. | .................. 73/38 |

* cited by examiner

Primary Examiner—Daniel S. Larkin
(74) Attorney, Agent, or Firm—Caesar, Rivise, Bernstein, Cohen & Pokotilow, Ltd.

(57) ABSTRACT

A check rod (1) for apparatus for measuring properties of longitudinally permeable rods, the check rod (1) comprising a hollow cylindrical body (2) having first, second and third transverse walls (4, 5, 6); a first chamber (17) defined by body (2) and the first and second transverse walls (4, 5); a second chamber (8) defined by body (2) and the second and third transverse walls (5, 6); at least one first ventilation window for air to flow laterally into chamber (7); at least one second ventilation window for air to flow laterally into chamber (8); and tubes (9, 10, 11) which are open at each end and provide for laminar air flow therethrough which is the only flow of air through the transverse walls, said tubes comprising at least one short tube (9) which passes through wall (4) and opens into chamber (7); at least one intermediate length tube (10) which passes through walls (5, 6) and opens into chamber (8), and at least one long tube (11) which passes through all walls (4, 5, 6) to allow passage of air through the full length of the check rod.

14 Claims, 2 Drawing Sheets

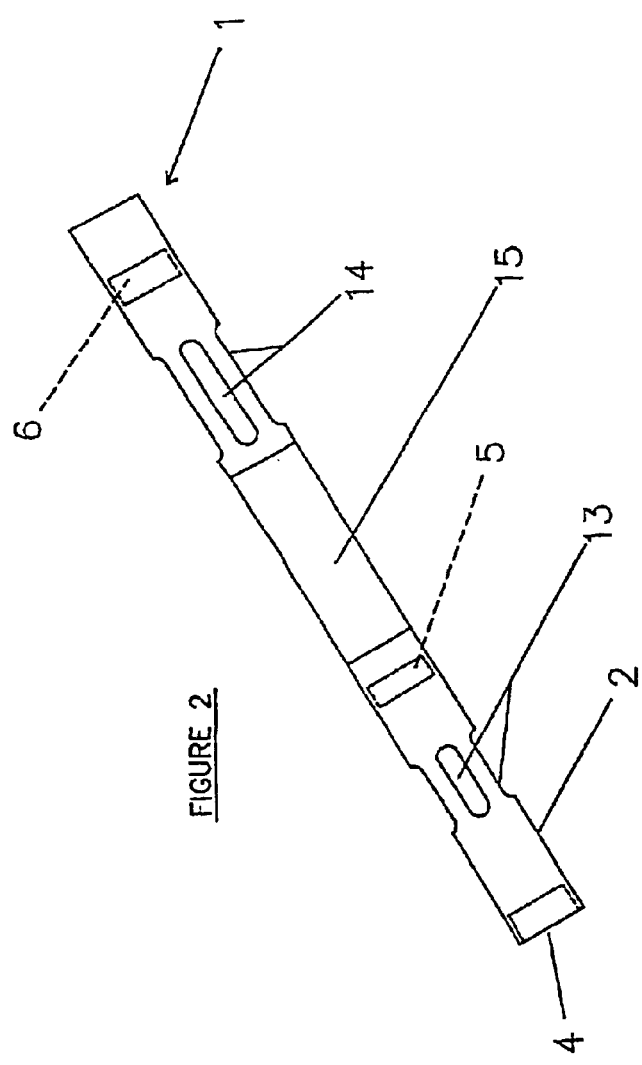
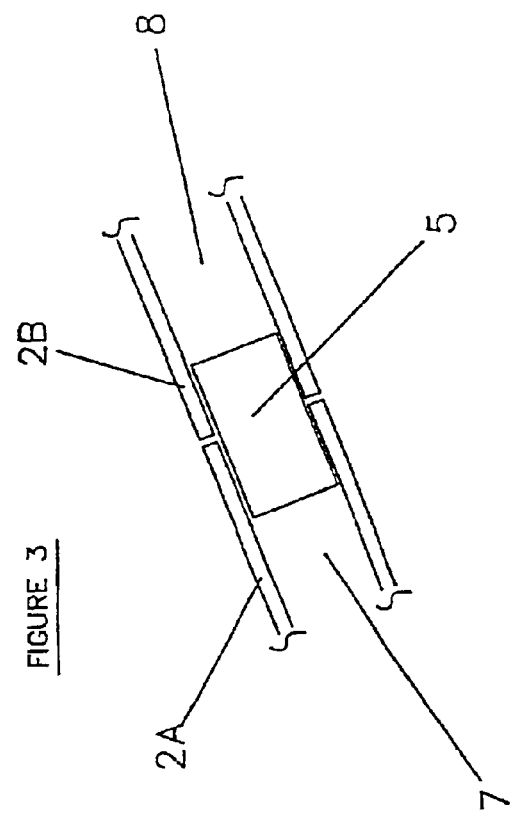

CHECK ROD

BACKGROUND OF THE INVENTION

The present invention relates to measurement of relevant properties of longitudinally air permeable rods, for example, cigarette rods, filter cigarette rods and filter rods and the like.

In order to monitor and maintain standards in mass produced smoking articles, such as cigarettes, filter cigarettes and filter rods, sample articles are taken from the production run and analysed. Important parameters that are measured include the pressure drop (or resistance to draw) weight, size and ventilation.

Conventionally, such properties are measured using fully automated testing machines. It is necessary to check that these machines are measuring correctly.

Conventionally, test machines have been checked using recognised standards. These are instrument specific and, being glass, are expensive and breakable. Known measurement check rods are not satisfactory as they have poor air flow properties which lead to unreliable pressure and ventilation results.

SUMMARY OF THE INVENTION

According to the present invention there is provided a check rod for apparatus for measuring properties of longitudinally permeable rods, the check rod comprising an elongate, substantially hollow, substantially cylindrical body; first, second and third transverse walls which are spaced longitudinally of the body; a first longitudinal chamber defined by the body and the first and second transverse walls; a second longitudinal chamber defined by the body and the second and third transverse walls; at least one first ventilation window for allowing air to flow from outside the body laterally into the first chamber; at least one second ventilation window for allowing air to flow from outside the body laterally into the second chamber; and tubes which are open at each end and provide for laminar air flow therethrough which is the only flow of air through the transverse walls, said tubes comprising at least one short laminar flow tube which passes through the first transverse wall and opens into the first chamber; at least one intermediate length laminar flow tube which passes through the first and second transverse walls and opens into the second chamber; and at least one long laminar flow tube which passes through the first, second and third transverse walls to allow passage of air through the full length of the check rod.

The laminar flow tubes function as laminar flow resistors. Each tube provides a standard resistance to flow of air through the tube. The number, size and arrangement of laminar flow tubes are chosen to provide predetermined values of resistance to air flow through the check rod, through the first transverse wall from the first chamber (when there is ventilation through the first window(s)), and through the first and second transverse walls from the second chamber (when there is ventilation through the second window(s)); the first window(s) and/or the second window(s) can be blocked (e.g. by wrapping) so that the check rod can be unventilated or ventilated at one or both ends, to correspond to the sample rods being tested. The check rod is placed in a measuring apparatus and the pressure drop measured; the measured values and predetermined values are compared to check that the machine is measuring correctly. The predetermined values may be calculated so that different check rods can be made for "high" pressure drop checks and "low" pressure drop checks, for example. The check rod that is used to check a machine is chosen so that it has a pressure drop in a range that is appropriate for the samples that are being tested.

Preferably, the laminar flow tubes are metal, for example thin-walled stainless steel tubes such as those used as syringe needles or canulae. Use of steel canulae has been found to give greater repeatability in the check rod value. The use of some alternative materials, such as ceramics, plastics or glass, is also possible. As a practical matter, however, metal is more suitable. Glass tubes are easily broken if the check rod is dropped or jolted in use, and it can be difficult to form ceramics or mould plastics into tubes of standard concentricity, i.e. with regular inner diameter or bore; variable or incorrect concentricity may lead to disrupted or turbulent (i.e. non laminar) air flow and hence to reduced accuracy and repeatability of check rod measurement.

Preferably, the check rod includes three short laminar flow tubes which pass through the first transverse wall and open into the first chamber. The use of three (or more) tubes ensures that the flow from the first chamber (when ventilated) through the first transverse wall is laminar and provides a readily measurable resistance to the flow, thereby ensuring accuracy and repeatability.

Preferably, the check rod includes two intermediate length laminar flow tubes which pass through the first and second transverse walls and open into the second chamber.

Preferably, the check rod includes two long laminar flow tubes which pass through the first, second and third transverse walls.

Preferably, the second transverse wall is nearer to the first transverse wall than to the third transverse wall. Preferably, the ratio of length of the second chamber to the first chamber is from about 3 or 4:1 to about 2:1. Preferably, the first chamber is about 20% to 35% of the total rod length.

Preferably, there is a plurality of first ventilation windows in substantially the same longitudinal position between the first and second transverse walls and equally spaced circumferentially. Such an arrangement advantageously provides steady flow of air into the first chamber (when ventilated). Preferably, there is a plurality of second ventilation windows in substantially the same longitudinal position between the second and third transverse walls and equally spaced circumferentially. Preferably, the second ventilation window(s) are adjacent or substantially adjacent to the third transverse wall, i.e. communicating with the end of the second chamber distal from the second wall. These arrangements advantageously provide steady flow of air into the second chamber (when ventilated). Preferably, the ventilation window(s) are significantly longer than the inner diameter or bore of the laminar flow tubes so as to reduce turbulence and maintain laminar flow. The window(s) also reduce the weight of the check rod.

The first and/or second ventilation window(s) may be, for example, gaps or slots in the hollow body. The gaps or slots etc. may be wholly or partially covered by an air permeable membrane, film or mesh which allows air to flow from outside the body into the first or second window.

Preferably, the cylindrical body includes a region that is dimensioned so that it has the same dimensions and roundness as that of an actual sample. The check rod may be used to check the roundness and size measurements as well as pressure drop. Preferably, the region is a central region, being located between the first and second ventilation windows in the region of the second transverse wall.

The check rods of the invention give reliable and repeatable check values for pressure drop, roundness, size etc. The check rods may be used, amongst other uses, to check calibration and/or to serve as means to compare test machines with one another.

It will be appreciated that check rods according to the invention may be manufactured to an exceptionally high standard and tolerances to ensure repeatability of results; such check rods would be suitable for use as (accredited) standards for calibration of the testing machine.

BRIEF DESCRIPTION OF THE DRAWINGS

Embodiments of the invention will now be illustrated with reference to the attached drawings in which:

FIG. 2 shows a top plan view of a check rod according to the invention (parts indicated with dotted lines and lead lines are located inside the standard and not normally visible in a plan view, being illustrated only to aid in understanding of the description); and FIG. 3 shows a longitudinal cross-section of part of the check rod of FIGS. 1 and 2.

DETAILED DESCRIPTION OF THE INVENTION

Figure 1:
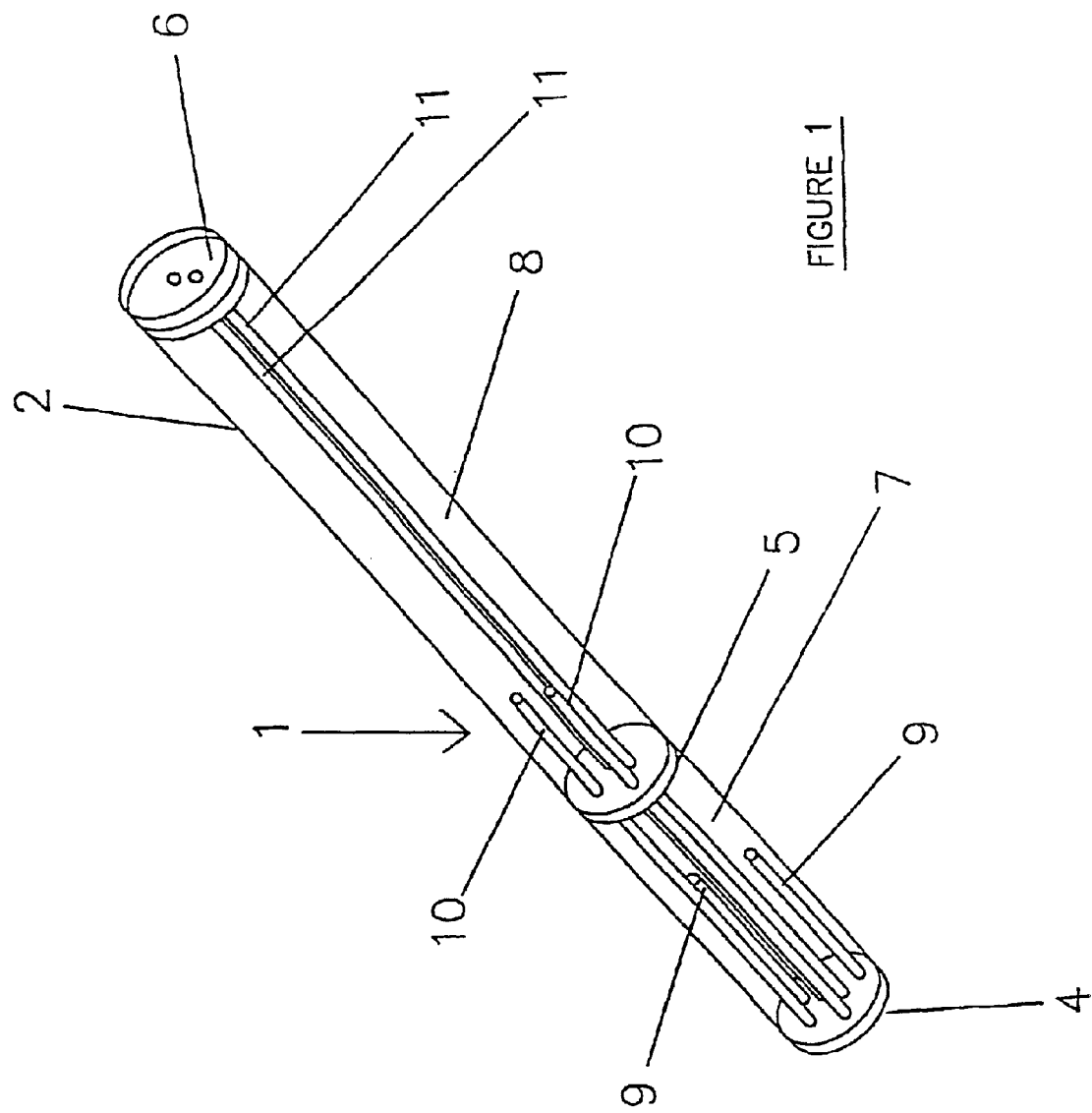
FIG. 1 shows a cut-away view of a check rod according to the invention.

FIG. 1 and FIG. 2 show a check rod 1 for checking an apparatus which measures pressure drop, size and roundness of longitudinal permeable rods, for example a sample cigarette, filter cigarette or filter rod. The check rod 1 includes a thin walled cylindrical body 2 made of a plastics material, such as DELRIN, TPX or PEEK. The plastics material provides a check rod which can be of the same dimensions as a cigarette sample and be of approximately the same weight.

The cylindrical body 2 has three circular transverse walls 4, 5, 6. Transverse wall 4 covers one end of cylindrical body 2 and will be termed the butt wall. Transverse wall 6 is located a short distance from the opposite end of cylindrical body 2, i.e. is recessed slightly within the cylindrical shell of body 2. Transverse wall 5 is located substantially three tenths of the way along the cylindrical body 2 measured from butt wall 4. The transverse walls 4, 5, 6 are made of the same plastics material as the cylindrical shell of the body 2 and are, at their circumferential edges, welded to the shell to form an airtight seal. The interior of the cylindrical shell of the body 2 and the transverse walls 4 and 5 define a first chamber 7 within the cylindrical body 2. The interior of the cylindrical shell of the body and the transverse walls 5 and 6 define a second chamber 8 within cylindrical body 2. Thus, first chamber 7 and second chamber 8 are separate from each other, separated by transverse wall 5.

As seen in FIG. 3, the thin-walled cylindrical body may be manufactured in two sections (2A and 2B), which are conveniently and firmly connected at and to transverse wall 5. It will be appreciated that by increasing the thickness of any or all of transverse walls 4, 5, 6 it is possible to increase the strength and robustness of the structure of the cylindrical body 2.

The check rod 1 includes seven laminar flow tubes 9, 10, 11 which are stainless steel metal canulae or thin-walled metal bodies. It will be appreciated that FIG. 1 shows only six laminar flow tubes (two each of laminar flow tubes 9, 10 and 11); the seventh tube is in this view obscured. The tubes may be made of any workable metal for example steel or copper.

The metal laminar flow tubes 9, 10 and 11 work as laminar flow resistors, that is each exerts a resistance to flow of fluid, e.g., air, through itself. The length and inner diameter or bore of the tubes depends on the desired resistance to flow value, and is chosen to suit the desired predetermined pressure drop value of the check rod 1. Examples are given below.

It will be appreciated that in the embodiments shown the metal canulae are straight, but it is possible to use different tubes, for example helical tubes, according to the standard pressure drop value which is required.

In the example shown in FIG. 1, three tubes 9 extend through butt wall 4 into chamber 7 to allow air to flow from the first chamber 7 through the butt wall 4 (when ventilated); two tubes 10 extend through butt wall 4, chamber 7, transverse wall 5 and into chamber 8 to allow air to flow from the second chamber 8 through the butt wall 4 (when ventilated); and two hollow metal extend the full length of the cylindrical body 2 from (and through) wall 4 to (and through) wall 6 to allow air to flow through the full check rod length.

The cylindrical body 2 has four first ventilation windows 13, which are four slots which communicate between the outside of the cylindrical body and first chamber 7, and four second ventilation windows 14, which are four slots which communicate between the outside of the cylindrical body 2 and chamber 8. Second ventilation windows 14 are located substantially adjacent the third transverse wall 6, as shown in FIG. 2. Each set of four slots is located a set distance from the butt end 4, and the slots in each set are spaced equidistantly about the circumference of the cylindrical body 2.

The check rod 1 includes a featureless cylindrical region 15 of the cylindrical shell between windows 13 and windows 14. This cylindrical region 15 is dimensioned to be the same (in terms of size, roundness etc.) as a sample cigarette, and can be used to calibrate the concentricity, roundness, etc. measurement functions of the measurement machine.

Check rods of the invention which are for use in machines for testing filter cigarettes are dimensioned and structural substantially the same as filter cigarettes. Thus such a check rod will be of length of about 84 mm. The transverse walls are positioned to correspond to the buccal end of a cigarette (first transverse wall 4), the join between filter tip and tobacco containing envelope (second transverse wall 5), and substantially at the remote end of the tobacco containing envelope (third transverse wall 6). Thus, the distance of the second transverse wall 5 from the first transverse wall 4 (buccal end)—i.e. the length of the first chamber—is about 20% to 35% of the total rod length (length of cylindrical body 2), preferably between 29% and 33% of the total rod length.

By way of further example, dimensions (in mm) of three check rods of different predetermined pressure drops are given in the following table. The check rods have the structure shown in FIGS. 1, 2 and 3.

TABLE 1

| Check Rod Example | 1 | 2 | 3 |
| --- | --- | --- | --- |
| Length of cylindrical body 2 (mm) | 84 | 84 | 84 |
| Diameter of cylindrical body 2 (mm) | 8.1 | 7.1 | 7.1 |
| Distance of transverse wall 5 from wall 4 (mm) | 26 | 26 | 26 |
| Distance of transverse wall 6 from wall 4 (mm) | 77 | 72 | 77 |
| Thickness of walls 4, 5, 6 (mm) | 1 | 1 | 1 |
| Number of windows 13, 14 | 4 | 4 | 4 |
| Length of windows 13, 14 (mm) | 11 | 11 | 11 |
| Width of windows 13, 14 (mm) | 1 | 1 | 1 |

TABLE 1-continued

| Check Rod Example | 1 | 2 | 3 |
|---|---|---|---|
| Distance of windows 13 from wall 4 at closest point (mm) | 10 | 10 | 10 |
| Distance of windows 14 from wall 4 at closest point (mm) | 63 | 63 | 63 |
| Length of cylindrical region 15 (mm) | 12 | 12 | 12 |
| Distance of cylindrical region 15 from wall 4 at closest point (mm) | 33 | 33 | 33 |
| Number of laminar flow tubes 9 | 3 | 3 | 3 |
| Length of tubes 9 (mm) | 14 | 23 | 21 |
| Number of laminar flow tubes 10 | 2 | 2 | 2 |
| Length of tubes 10 (mm) | 34 | 27 | 29 |
| Number of laminar flow tubes 11 | 2 | 2 | 2 |
| Length of tubes 11 (mm) | 78 | 73 | 78 |
| *Weight (g) | 2.2 | 1.9 | 1.9 |

In Examples 1, 2 and 3 laminar flow tubes 9, 10, 11 are stainless steel of inner diameter 0.55 mm.

The weight of the check rod is the same as an actual sample rod, and thus, the rod may be used to check sample weighing measurements.

In use, the check rod 1 is placed in the sample head of a measuring machine, for example, a QTM5, QTM5U or QTM6 machine, such as those manufactured by Filtrona Instruments & Automation Limited of the UK for measuring the pressure drop (or resistance to draw) and other parameters of sample cigarettes, filter cigarettes or filter rods.

Pressure drop measuring machines are well known in the art. A pressure drop measuring machine holds a sample cigarette (generally comprising filter tip and tobacco containing envelope) in a sample head and draws a flow of air through the sample. The sample head is constructed so that a first air-tight seal can be made around the circumference walls of the filter tip, and a second air-tight seal can be made around the circumference walls of the tobacco containing envelope. The seals can be opened and closed independently of each other. A sample head of this type can be used in the determination of the five following values necessary for testing/quality control:

1] $Pd_o$. This is the total pressure drop measured across the filter cigarette with the seal around the filter tip open (i.e. with air flow into the sample via any filter tip ventilation) and the seal around the tobacco envelope open (i.e. with air flow into the sample through the tobacco envelope walls).

2] $Pd_c$. This is the total pressure drop measured across the filter cigarette with the seal around the filter tip closed (i.e. with no air flow into the sample via filter tip ventilation) and the seal around the tobacco envelope open.

3] "Tip ventilation" or "filter ventilation". This is the % of total air flow through the cigarette sample which results from air flow into the filter tip via its ventilation (e.g. pores or holes in the filter tip walls).

4] "Envelope ventilation" or "paper ventilation". This is the % of total air flow through the cigarette sample which results from air flow through the wall (e.g. the paper) which surrounds the tobacco column.

5] "Total ventilation". This is generally calculated as the sum of tip ventilation and envelope ventilation: it is the % of total air flow through the cigarette sample which results from air flow through the wall of the filter plus air flow through the wall surrounding the tobacco.

$Pd_o$ and $Pd_c$ are found by pulling a constant flow of air through the sample and measuring the pressure drop across the sample with the relevant seals either open or closed. Tip and envelope ventilation are determined by pulling a constant air flow through the sample and, with the relevant seal in place, measuring the air flow into the tip (or envelope) region through the wall of the filter (or envelope) using a laminar flow element. The constant air flow is then switched to pass through the laminar flow element; the difference in measured values can be used to calculate the % of total flow laterally into the tip or through the envelope. Total ventilation is calculated as the sum of tip and envelope ventilation. The five values are derived from measurements found using three air flow pathways. These are a pathway through the walls of the filter tip and to the buccal end of the sample (which corresponds to tip ventilation air flow); a pathway through the walls of the tobacco containing envelope and to the buccal end of the sample (which corresponds to envelope ventilation air flow); and a pathway across the sample cigarette as a whole (i.e. from the mouth or buccal end to the remote end). The last pathway corresponds to air flow drawn in through the remote end and to the mouth end. This last air flow contributes to the $Pd_o$ and $Pd_c$ values.

Before and/or during measurement of samples it is desirable to check that the machine is giving appropriate values. This is done using the check rod.

The check rod 1 provides three air flow pathways of standard, known resistance value, which correspond to the pathways in a sample cigarette that are described above. These are as follows. Windows 13, first chamber 7 and tubes 9 of the standard 1 correspond to the air flow pathway across the filter tip of a sample cigarette within the sample head; that is, the resistance to air flow through laminar flow tubes 9 corresponds to the pressure drop across the filter tip of a sample cigarette. Windows 14, chamber 8 and tubes 10 of the standard 1 correspond to the air flow pathway across the tobacco envelope of a cigarette sample; that is, the resistance to air flow through laminar flow tubes 10 corresponds to the pressure drop across the tobacco envelope. Finally, tubes 11 of the standard 1 correspond to the air flow pathway for pressure drop across a complete filter cigarette sample. In order to check the values for $Pd_o$ and $Pd_c$ this pathway is used in combination with the tobacco envelope air flow pathway (14, 8, 10) to check $Pd_c$; and in combination with the tobacco envelope air flow pathway (14, 8, 10) and filter tip pathway (13, 7, 9) to check $Pd_o$. With the check rod 1 in place in the sample head the values are derived by a QTM5 or QTM5U pressure drop machine (in the same way as it would measure a sample) and the derived value compared with the known value of the check rod for each value. If there is any variation from the known value, the operator is alerted and can check for a fault.

The check rod may be used in machines for testing the pressure drop across filter rods such as the QTM6. In this case, the important measurement is pressure drop across the whole rod.

The QTM5, QTM5U and QTM6 machines measure the size and roundness of samples using a laser. The region 15 of the check rod is located so that, when placed in the QTM5 or QTM5U machine, this is located under the laser measurement system. With the check rod 1 in place the size, roundness, etc. of the region 15 of the rod is measured by the QTM5 or QTM5U machine (as it would measure a sample) and the measured value compared with the known value of the check rod. If there is any variation from the known value the operator is alerted and can check for a fault.

The check rod may be used in the course of sampling. The check rod may be put directly into the measuring/testing head of the machine in place of a sample rod, or it may be placed in amongst a number of sample rods, for example in the inlet hopper of the test machine, so that it enters the testing or measurement head in the course of automated testing.

What is claimed is:

1. A check rod for apparatus for measuring properties of longitudinally permeable rods, the check rod comprising an elongate, substantially hollow, substantially cylindrical body; first, second and third transverse walls which are spaced longitudinally of the body; a first longitudinal chamber defined by the body and the first and second transverse walls; a second longitudinal chamber defined by the body and the second and third transverse walls; at least one first ventilation window for allowing air to flow from outside the body laterally into the first chamber; at least one second ventilation window for allowing air to flow from outside the body laterally into the second chamber; and tubes which are open at each end and provide for laminar airflow therethrough which is the only flow of air through the transverse walls, said tubes comprising at least one short laminar flow tube which passes through the first transverse wall and opens into the first chamber; at least one intermediate length laminar flow tube which passes through the first and second transverse walls and opens into the second chamber; and at least one long laminar flow tube which passes through the first, second and third transverse walls to allow passage of air through a full length of the check rod.

2. A check rod according to claim 1 in which the laminar flow tubes are metal.

3. A check rod according to claim 1 including three short laminar flow tubes.

4. A check rod according to claim 1 including two intermediate laminar flow tubes.

5. A check rod according to claim 1 including two long laminar flow tubes.

6. A check rod according to claim 1 further including a region that is dimensioned so that said region has identical dimensions and roundness as the longitudinally permeable rods.

7. A check rod according to claim 1 including a plurality of first ventilation windows in substantially identical longitudinal position between the first and second transverse walls and equally spaced circumferentially.

8. A check rod according to claim 7 wherein the first ventilation windows are significantly longer than an inner diameter of the laminar flow tubes.

9. A check rod according to claim 1 including a plurality of second ventilation windows in substantially identical longitudinal position between the second and third transverse walls and equally spaced circumferentially.

10. A check rod according to claim 9 wherein the second ventilation windows are substantially adjacent the third transverse wall.

11. A check rod according to claim 10 wherein the second ventilation windows are significantly longer than an inner diameter of the laminar flow tubes.

12. A check rod according to claim 1 wherein the second transverse wall is nearer to the first transverse wall than to the third transverse wall.

13. A check rod according to claim 1 wherein a ratio of a length of the second chamber to a length of the first chamber is from about 3 or 4:1 to about 2:1.

14. A check rod according to claim 1 wherein a length of the first chamber is about 20% to 35% of the full rod length.

* * * * *